United States Patent [19]

Ramezanian

[11] Patent Number: 5,194,651
[45] Date of Patent: Mar. 16, 1993

[54] TOSYLATION OF ALCOHOLS

[75] Inventor: Merrikh Ramezanian, Baton Rouge, La.

[73] Assignee: Ethyl Corporation, Richmond, Va.

[21] Appl. No.: 827,586

[22] Filed: Jan. 29, 1992

Related U.S. Application Data

[63] Continuation of Ser. No. 640,845, Jan. 14, 1991, abandoned.

[51] Int. Cl.$^5$ .................. C07C 303/00; C07C 307/00; C07C 311/00
[52] U.S. Cl. ....................................... 558/46; 558/51; 558/52; 558/53; 558/56; 558/57
[58] Field of Search ...................... 558/56, 46, 51, 52, 558/53, 57

[56] References Cited

PUBLICATIONS

Hoffman J. Chem. Soc. (London) (1965) 6748–6753.
Foldi Berichte, 60B, 656 (1927).

*Primary Examiner*—Alan Siegel
*Attorney, Agent, or Firm*—Richard J. Hammond

[57] ABSTRACT

A process is disclosed for the preparation of aliphatic toluenesulfonates. The process comprises reacting a solution of an aliphatic alcohol and an alkali metal hydroxide in a solution of an aprotic solvent with toluenesulfonyl chloride for from about 1 to about 12 hours and forming said aliphatic toluenesulfonate. These compounds are useful intermediates in the preparation of complex organic molecules.

8 Claims, No Drawings

TOSYLATION OF ALCOHOLS

This is a continuation of copending application Ser. No. 07/640,845 filed on Jan. 14, 1991, now abandoned.

FIELD OF THE INVENTION

The invention relates to an improved method for preparing p-toluenesulfonic acid esters. More particularly, the invention relates to an improved process for preparing aliphatic toluenesulfonates from the reaction of aliphatic alcohols and toluenesulfonyl chloride.

BACKGROUND OF THE INVENTION

The preparation of ester derivatives of sulfonic acids can be carried out by heating the solid sodium salt of the acid with dimethyl or diethyl sulfate.

Sulfonic acid esters are most frequently prepared by treatment of the corresponding halides with alcohols in the presence of a base. This method is used for the conversion of alcohols to tosylates, brosylates and similar sulfonic acid esters. The alcohols may be either aliphatic or aromatic. The base is usually pyridine which functions as a nucleophilic catalyst. See Frieser and Frieser, Ref. 411, Vol. 1, page 1180 (1967).

The aryl sulfonates are sometimes useful for the purposes of identification or as a leaving group in nucleophilic substitution reactions.

While the prior art methods for the preparation of these esters are satisfactory, they provide long reaction times and tedious workup. Additionally, since aqueous separations are required, isolation of the desired product is inconvenient. Yields of the esters are adversely affected.

It is desirable, therefore, to have available a process for producing these toluenesulfonic acid esters that allows easy separation of the product in increased yields and shorter reaction times.

DESCRIPTION OF THE PREFERRED EMBODIMENTS

The process of the present invention utilizes toluenesulfonyl chloride (tosyl chloride) as one of the main reactants. The compound is prepared by the reaction of toluene with fuming sulfuric acid. The sulfonic acid either as the free acid or as the salt is subsequently converted into the acid chloride by reaction with a phosphorous halide.

The aliphatic toluenesulfonates are prepared by the reaction of tosyl chloride with a solution of an aliphatic alcohol and an alkali metal hydroxide. The aliphatic alcohols of use in this process are those of the formulas:

$CH_2=CH-(CH_2)_nOH$, where n is 1 to 6;

$HO[(CH_2)_mO]_pH$, where m is 1 to 4 and p is from 1 to 2000; and

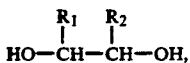

where $R_1$ and $R_2$ are the same or different and are $C_1$ to $C_6$ linear or branched alkyl (sometimes referred to herein as "alkyl") and phenyl or naphthyl unsubstituted or substituted with $C_1$ to $C_6$ linear or branched alkyl, $C_1$ to $C_6$ linear or branched alkoxy, halo (fluoro, chloro, bromo or iodo) or carboxylic acid ester.

In the above listed aliphatic alcohols, it is preferred that n and m are 1 to 3, p is 1 to 1000, and $R_1$ and $R_2$ are the same or different and are methyl, ethyl, n-propyl, i-propyl, phenyl, naphthyl unsubstituted or substituted with methyl, ethyl, n-propyl, i-propyl, methoxy, ethoxy, n-propyloxy or i-propyloxy.

In the process of the present invention, hydrogen chloride is a by-product of the reactions of tosyl chloride with the aliphatic alcohol. While the prior art prefers to use pyridine as an acid acceptor in similar reactions, the process of the present invention utilizes an alkali metal hydroxide such as potassium or sodium hydroxide. The use of this compound in up to 2 molar excess favors the reaction by an apparent catalytic effect as well as by the simple chemical combination with by-product HCl. Thus, it has been discovered that a ratio of aliphatic alcohol:alkali metal hydroxide:toluenesulfonyl chloride of 1:2x:1x where x is the number of hydroxy groups is useful in the present process.

In carrying out the reaction, the reactants are dissolved in an insert aprotic solvent, i.e., one that does not react with any of the reactants or products of the reaction. These inert, aprotic solvents include the dialkyl ethers and aromatic hydrocarbons. Preferably, the solvents are dialkyl ether, benzene or toluene.

The reaction is typically carried out at room temperature and produces the desired aliphatic toluenesulfonate in good yields in from about 1 to about 12 hours, preferably about 1 to about 6 hours. The acid chloride produced is usually an oil which is usually soluble in ether. Advantageously, no water is required for separation and/or isolation of the final product.

The aliphatic toluenesulfonates prepared by the process of the present invention are useful intermediates in the preparation of a wide variety of organic compounds.

The following examples are intended for the purpose of illustration only and should not be regarded as limiting the invention in any way.

EXAMPLES

EXAMPLE 1

Tosylation of allyl alcohol and 3-butene-1-01

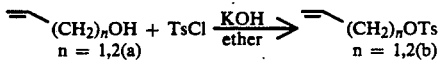

p-Toluenesulfonyl chloride (TsCl) (0.i mole) was added to a solution of allyl alcohol (0.1 mole) in ether (250 mL). Ground potassium hydroxide (10 g, 0.175 mole) was added to the mixture at 5° C with stirring. Stirring was continued at this temperature for 2 hours. After filtration, ether was evaporated with rotary evaporator. A colorless liquid was obtained. Distillation under lower pressure gave colorless liquid (90% for 1 b, 81% for 2 b).

1 b: $^1$H-NMR(CDCl$_3$): δ, 7.8(d, 2H, aromatic ring), 7.35(d, 2H, aromatic ring), 5.8(m, 1H, =CH), 5.3(d, 2H, CH$_2$=), 4.55(d, 2H, CH$_2$O) and 2.45(s, 3H, CH$_3$)$^{13}$C-NMR(CDCl$_3$): δ; 145, 133, 130, 128, 120, 71, 22 ppm.

2b: $^1$H-NMR(CDCl$_3$):δ; 7.79(d, 2H, aromatic ring), 7.34(d, 2H, aromatic ring), 5.68(m, 1H, =CH), 5.12(m, 2H, CH$_2$=), 4.09(t, 2H, CH$_2$O), 2.52(s, 3H, CH$_3$), and 2.45(m, 2H, CH$_2$).

Example 2

Tosylation of polyethylene glycol (PEG)

Excess TsCl (47.5, 0.25 mole) was added to the solution of polyethylene glycol (MW, 300; l5 g, 0.05 mole) in 500 mL anhydrous ether under argon at room temperature. Then potassium hydroxide (25 g) was added and stirring was continued at room temperature under argon for 2 days. After filtration and concentration, the crude oil was purified by column chromatography over silicon gel to afford 13g (42%) of pure product. 'H-NMR(CDCl$_3$): δ; 7.84(d, 2H, aromatic ring), 7.36(d, 2H, aromatic ring), 4.18(t, 2H, CH$_2$), 3.67(t, 4H, CH$_2$), 3.42(m, all CH$_2$ in the middle of polymer), and 2.48(s, 6H, CH$_3$); elemental analysis for tosylated PEG(avg. MW =300): Calc; C, 52.89; H, 6.51 S, 10.52; Found, C, 52.80; H, 6.46; S, 11.17

Example 3

Synthesis of 1,2-diphenylethylene bistoluene-p-sulfonate

Potassium hydroxide (400 mg, 7.0 mmole) was added to a solution of 1,2-diphenylethane-1,2-diol (l40 mg, 0.65 mmole) in dry ether (30 mL). TsCl (286 mg, 1.5 mmole) was added. The reaction was completed after 1 hour with stirring under N$_2$ atmosphere at RT. A white solid was obtained. The white solid was filtered and washed with dichloromethane. The combined filtrate was concentrated, Recrystallization with methylene chloride and hexane gave the crystalline solid (1.4 g, 44.6%), mp, 110-112 (decomposed), 'H-NMR(CDCl$_3$) δ, 2.39(s, 6H CH$_3$), 5.61(s, 2H, CH), 6.89-7.55(m, 18H, ArH).

Example 4

Comparative

General method for preparation of tosylate

To a solution of 1 (20.0 g, 120 mmole) in dry pyridine (60 mL) was added, at −10° C., p-TsCl (25.0 g, 130 mmole) at room temperature for 16 hours, hydrolyzed with 10% HCl, extracted with chloroform, dried over sodium sulfate, and worked up in the usual manner. The crude product was crystallized from ether to give the tosylate of 1 (35.8 g, 92%).

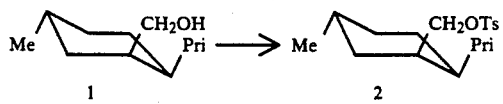

I claim:

1. In a process for preparing aliphatic toluenesulfonates by the reaction of a toluenesulfonyl chloride with an aliphatic alcohol and an alkali metal hydroxide in a solution of an aprotic solvent, the improvement consisting of separating the aliphatic toluenesulfonate from said solution and then purifying the aliphatic toluenesulfonate, the separating and purifying carried out in the absence of water.

2. The process according to claim 1 wherein said aliphatic alcohol is CH$_2$=CH-(CH$_2$)$_n$OH, where n is 1 to 6.

3. The process according to claim 1 wherein said aliphatic alcohol is HO[(CH$_2$)$_m$O]$_p$H, where m is 1 to 4 and p is form 1 to 2000.

4. The process according to claim 1 wherein said aliphatic alcohol

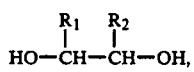

where R$_1$ and R$_2$ are the same or different and are C$_1$ to C$_6$ linear or branched alkyl and phenyl or naphthyl unsubstituted or substituted with C$_1$ to C$_6$ linear or branched alkyl, C$_1$ to C$_6$ linear or branched alkoxy, halo (fluoro, chloro, bromo or iodo) or carboxylic acid ester.

5. The process according to claim 1 wherein said aprotic solvent is a dialkyl ether or aromatic hydrocarbon.

6. The process according to claim 1 wherein said reaction is carried out from about 1 to about 6 hours.

7. The process according to claim 6 wherein said alkali metal hydroxide is sodium hydroxide or potassium hydroxide.

8. The process according to claim 7 wherein the mole ratio of aliphatic alcohol:alkali metal hydroxide:toluenesulfonyl chloride is 1:2x:1x where x is the number of hydroxy groups.

* * * * *